(12) United States Patent
Hellendahl et al.

(10) Patent No.: US 6,444,674 B1
(45) Date of Patent: Sep. 3, 2002

(54) SUBSTITUTED PYRIMIDINE COMPOUNDS AND THE USE THEREOF

(75) Inventors: Beate Hellendahl, Schifferstadt; Annegret Lansky, Darmstadt, both of (DE); Rainer Munschauer, Shrewsbury (MA); Siegfried Bialojan, Oftersheim (DE); Liliane Unger, Ludwigshafen (DE); Hans-Jürgen Teschendorf, Dudenhofen (DE); Karsten Wicke, Altrip (DE); Karla Drescher, Dossenheim (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/940,937

(22) Filed: Aug. 29, 2001

Related U.S. Application Data

(62) Division of application No. 08/765,292, filed on Jan. 14, 1997, now Pat. No. 6,342,604.

(30) Foreign Application Priority Data

Jul. 15, 1994 (DE) ........................ P 44 25 143

(51) Int. Cl.⁷ ................. C07D 239/28; A61K 31/506; A61P 25/16

(52) U.S. Cl. ................ 514/252.14; 544/295; 544/296; 544/330; 544/331; 544/322; 544/180

(58) Field of Search ................ 544/295, 180, 544/330, 331, 322, 296; 514/252.14

(56) References Cited

U.S. PATENT DOCUMENTS 5,244,894 A * 9/1993 George et al. ............ 544/295

* cited by examiner

Primary Examiner—Richard L. Raymond
Assistant Examiner—Venkataraman Balasubrasubramanian
(74) Attorney, Agent, or Firm—Keil & Weinkauf

(57) ABSTRACT

The present invention relates to the use of pyrimidine compounds of the following formula:

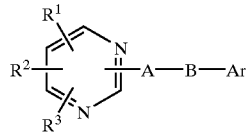

where $R^1$, $R^2$, $R^3$, A, B and Ar have the meanings indicated in the description. The compounds according to the invention have a high affinity for the dopamine $D_3$ receptor and can therefore be used to treat disorders which respond to dopamine $D_3$ ligands.

15 Claims, No Drawings

SUBSTITUTED PYRIMIDINE COMPOUNDS AND THE USE THEREOF

This is a Divisional application of application Ser. No. 08/765,292, filed on Jan. 14, 1997, under Section 371 which is U.S. Pat. No. 6,342,604

The invention relates to substituted pyrialidine compounds and to the use of such compounds. Said compounds have valuable therapeutic properties and can be used in particular to treat disorders which respond to dopamine $D_3$ ligands.

Compounds which are of the type under discussion here and have physiological activity have in some cases been disclosed. Thus, DE 21 39 082 and DE 22 58 561 describe pyrimidine derivatives and pyrimidone derivatives with basic substituents as drugs for lowering blood pressure. These pyrimidine and pyrimidone derivatives have the formulae:

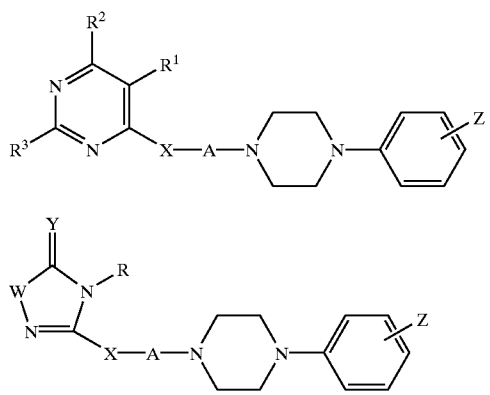

where in (A) X is, inter alia, sulfur, A is $C_1$–$C_6$-alkylene, and $R^1$, $R^2$, $R^3$ and Z are various substituents. In (B), X and Y are each oxygen or sulfur, A is $C_2$–$C_6$-alkylene and R and Z are various substituents.

Neurons receive their information inter alia via G protein-coupled receptors. There are numerous substances which exert their effect via these receptors. One of them is dopamine.

Confirmed findings on the presence of dopamine and its physiological function as neurotransmitter have been published. Cells which respond to dopamine are connected with the etiology of schizophrenia and Parkinson's disease. These and other disorders are treated with drugs which interact with dopamine receptors.

By 1990, two subtypes of dopamine receptors had been clearly defined pharmacologically, namely $D_1$ and $D_2$ receptors.

Sokoloff et al., Nature 1990, 347: 146–151, found a third subtype, namely $D_3$ receptors. They are expressed mainly in the limbic system. The $D_3$ receptors differ structurally from the $D_1$ and $D_2$ receptors in about half the amino-acid residues.

The effect of neuroleptics has generally been ascribed to their affinity for $D_2$ receptors. Recent receptor-binding studies have confirmed this. According to these, most dopamine antagonists, like neuroleptics, have high affinity for $D_2$ receptors but only low affinity for $D_3$ receptors.

We have now found, surprisingly, that certain pyrimidine compounds have a high affinity for the dopamine $D_3$ receptor and a low affinity for the $D_2$ receptor. They are thus selective $D_3$ ligands.

The present invention therefore relates to the use of pyrimidine compounds of the general formula I:

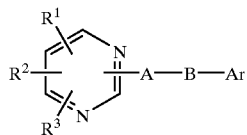

where

A is $C_1$–$C_{18}$-alkylene which may comprise at least one group selected from O, S, $NR^4$, $CONR^4$, $NR^4CO$, COO, OCO and a double or triple bond, B is

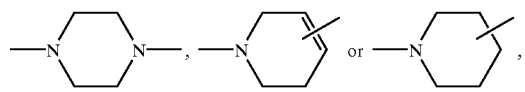

$R^1$, $R^2$, $R^3$ are selected, independently of one another, from H, halogen, $OR^4$, $NR^4R^5$, $SR^4$, $CF_3$, CN, $CO_2R^4$ and $C_1$–$C_8$-alkyl which is unsubstituted or substituted by OR, $OC_1$–$C_8$-alkyl or halogen, $R^4$ is H, $C_1$–$C_8$-alkyl which is unsubstituted or substituted by OR, $OC_1$–$C_8$-alkyl or halogen, $R^5$ has the meanings indicated for $R^4$ or is $COR^4$ or $CO_2R^4$;

Ar is phenyl, pyridyl, pyrimidyl or triazinyl, where Ar may have from one to four substituents which are selected, independently of one another, from $OR^5$, $C_1$–$C_8$-alkyl, $C_2$–$C_6$-alkenyl, $C_2$–$C_6$-alkynyl, halogen, CN, $CO_2R^4_1$, $NO_2$, $SO_2R^4$, $SO_3R^4$, $NR^4R^5$, $SO_2NR^4R^5$, $SR^4$, $CF_3$, $CHF_2$, a 5- or 6-membered carbocyclic aromatic or non-aromatic ring and a 5- or 6-membered heterocyclic aromatic or non-aromatic ring having 1 to 3 hetero atoms which are selected from O, S and N, where the ring may be unsubstituted or substituted by $C_1$–$C_8$-alkyl, Hal, $OC_1$–$C_8$-alkyl, OH, $NO_2$, $CF_3$, and where Ar may also be fused to a carbocyclic or heterocyclic ring of the type defined above, and the salts thereof with physiologically tolerated acids for producing a pharmaceutical composition for treating disorders which respond to dopamine $D_3$ receptor antagonists or agonists.

The invention also relates to the pyrimidine compounds of the formula I'

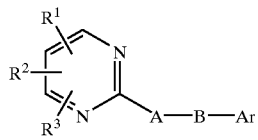

where

A, B, Ar, $R^1$, $R^2$ and $R^3$ have the meanings stated in claims 1 to 8, and the salts thereof with physiologically tolerated acids, excepting the compounds of the formula

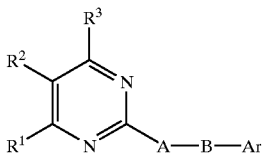

where $R^1$ is OH or SH, $R^2$ and $R^3$ are, independently of one another, H, $C_1$–$C_8$-alkyl, $OC_1$–$C_6$-alkyl, $SC_1$–$C_6$-alkyl, $CO_2H$, OH, SH, $NR^4R^5$ or halogen, where $R^4$ and $R^5$ are H or $C_1$–$C_6$-alkyl, A is $SC_1$–$C_6$-alkylene, $NHC_1$–$C_6$-alkylene or $N(C_1$–$C_6$-alkyl)-$C_1$–$C_6$-alkylene, B is

and Ar is phenyl
which may have one or more substituents selected from $C_1$–$C_4$-alkyl, $OC_1$–$C_4$-alkyl, $SC_1$–$C_4$-alkyl, $NO_2$, $CF_3$, F, Cl or Br.

The compounds used according to the invention are selective dopamine $D_3$ receptor ligands which intervene regioselectively in the limbic system and, because of their low affinity for the $D_2$ receptor, have fewer side effects than classical neuroleptics, which are $D_2$ receptor antagonists. The compounds can therefore be used to treat disorders which respond to dopamine $D_3$ receptor antagonists or agonists, eg. for treating disorders of the central nervous system, in particular schizophrenia, depression, neuroses and psychoses. They can additionally be used to treat sleep disorders and nausea and as antihistamines.

Within the scope of the present invention, the following terms have the meanings indicated below: alkyl (also in radicals such as alkoxy, alkylamino, etc.) means a straight-chain or branched alkyl group having 1 to 8 carbon atoms, preferably 1 to 6 carbon atoms and, in particular, 1 to 4 carbon atoms. The alkyl group can have one or more substituents which are selected, independently of one another, from OH and $OC_1$–$C_8$-alkyl.

Examples of an alkyl group are methyl, ethyl, n-propyl, i-propyl, n-butyl, isobutyl, t-butyl, etc.

Alkylene stands for straight-chain or branched radicals having, preferably, 2 to 15 carbon atoms, particularly preferably 3 to 10 carbon atoms.

The alkylene groups may comprise at least one of the abovementioned groups. This can—just like the double or triple bond mentioned—be arranged in the alkylene chain at any point or at the end of the chain so that it connects the chain to the pyrimidine residue. The latter is preferred. When the alkylene group comprises a double or triple bond, it has at least three carbon atoms in the chain.

Halogen is F, Cl, Br, I and, in particular, Cl, Br, I.

$R^1$, $R^2$ and $R^3$ are preferably, independently of one another, H, $C_1$–$C_8$-alkyl, $NR^4R^5$, $SR^4$ or $OR^4$, where $R^4$ and $R^5$ are, independently of one another, H or $C_1$–$C_8$-alkyl.

Ar can have one, two, three or four substituents, preferably one or two substituents, which are in each case in the m position. They are preferably selected independently from halogen, $CF_3$, $CHF_2$, CN, $NO_2$, $OR^4$, $NR^4R^5$, $C_1$–$C_8$-alkyl, $OC_1$–$C_8$-alkyl, phenyl and $SR^4$, where $R^4$ and $R^5$ are H or $C_1$–$C_8$-alkyl. If one of the substituents is $C_1$–$C_8$-alkyl, a branched group and, in particular, isopropyl or t-butyl is preferred.

Ar preferably has at least one substituent and is, in particular,

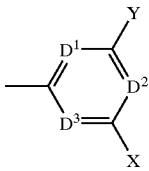

where $D^1$, $D^2$ and $D^3$ are, independently of one another, CR or N, and R, S and Y are H or have the meanings indicated above or below.

Ar is preferably unsubstituted or substituted phenyl, 2-, 3- or 4-pyridinyl or 2-, 4(6)- or 5-pyrimidinyl.

When one of the substituents of the radical Ar is a 5- or 6-membered heterocyclic ring, examples thereof are a pyrrolidine, piperidine, morpholine, piperazine, pyridine, 1,4-dihydropyridine, pyrimidine, triazine, pyrrole, thiophene, thiazole, imidazole, oxazole, isoxazole, pyrazole or thiadiazole residue.

When one of the sustituents of the radical Ar is a carbocyclic radical, it is, in particular, a phenyl, cyclopentyl or cyclohexyl radical.

When Ar is fused to a carbocyclic or heterocyclic radical, it is, in particular, a naphthalene, di- or tetrahydronaphthalene, quinoline, di- or tetrahydroquinoline, indole, dihydroindole, benzimidazole, benzothiazole, benzothiadiazole, benzopyrrole or benzotriazole residue.

A preferred embodiment comprises the compounds of the formula I where A is $C_1$–$C_{10}$-alkylene which may comprise at least one group selected from O, S, $NR^3$, cyclohexylene and a double or triple bond.

Another preferred embodiment comprises use of the compounds of the formula I where $R^1$, $R^2$ and $R^3$ are, independently of one another, H, $C_1$–$C_8$-alkyl which can be unsubstituted or substituted by OH, $OC_1$–$C_8$-alkyl or OH [sic], or OH, $OC_1$–$C_8$-alkyl, $SR^4$ or $NR^4R^5$, where $R^4$ and $R^5$ are, independently of one another, H or $C_1$–$C_8$-alkyl;

Ar is phenyl, pyridyl or pyrimidyl which may have one, two, three or four substituents selected from H. $C_1$–$C_8$-alkyl which may be substituted by OH, $OC_1$–$C_8$-alkyl or halogen, or $OR^4$ where $R^4$ is , $C_1$–$C_8$-alkyl which may be substituted by OH, $OC_1$–$C_8$-alkyl or halogen, or $CHF_2$, $CF_3$, CN, halogen, $C_2$–$C_6$-alkenyl, $C_2$–$C_6$-alkynyl, $C_1$–$C_6$-cyclohexyl [sic], phenyl, naphthyl and a 5- or 6-membered heterocyclic aromatic radical with 1 to 3 hetero atoms selected from O, N and S.

Another preferred embodiment comprises use of the compounds of the formula I where B is

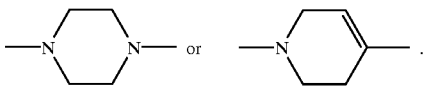

Another preferred embodiment is the use of the compounds of the formula I where Ar is phenyl which has one to four substituents which are selected, independently of one another, from H, $C_1$–$C_8$-alkyl which may be substituted by OH, $OC_1$–$C_8$-alkyl or halogen, or phenyl, naphthyl, pyrrolyl, CN, $NO_2$, $CF_3$, $CHF_2$, halogen, $SO_2R^4$ or $SR^4$ where $R^4$ is H or $C_1$–$C_8$-alkyl, or where the substituents are selected, independently of one another, from $C_1$–$C_8$-alkyl, phenyl, $CF_3$, $CHF_2$, CN, $NO_2$, halogen, $OC_1$–$C_8$-alkyl or $SR^4$ where $R^4$ is H or $C_1$–$C_8$-alkyl, and Y is H, $C_1$–$C_8$-alkyl, Hal or $CF_3$.

Another preferred embodiment is the use of compounds of the formula I where Ar is pyrimidinyl which has one to three substituents which are selected, independently of one another, from H, $C_1$–$C_8$-alkyl, phenyl, naphthyl, $C_3$–$C_6$-cyclohexyl [sic], OH, $OC_1$–$C_8$-alkyl, halogen, CN, $NO_2$, $CF_3$, $CHF_2$ and a 5- or 6-membered heterocyclic aromatic or non-aromatic radical with 1 to 3 hetero atoms selected from O, N and S.

Another preferred embodiment is the use of compounds of the formula I where Ar is pyridinyl which has one to four substituents which are selected, independently of one another, from H, $C_1$–$C_8$-alkyl, phenyl, naphthyl, OH, $OC_1$–$C_8$-alkyl, halogen, $CF_3$, CN, $C_2$–$C_6$-alkenyl, $C_2$–$C_6$-alkynyl and a 5- or 6-membered heterocyclic aromatic radical with 1 to 3 hetero atoms selected from O, N and S.

The invention also embraces the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung, Volume 10, pages 224 et seq., Birkhauser Verlag, Basle and Stuttgart, 1966.

The compounds of the formulae [sic] I may have one or more centers of asymmetry. The invention therefore includes not only the racemates but also the relevant enantiomers and diastereomers. The invention also includes the tautomeric forms in each case.

The compounds of the formula I' can be prepared by methods similar to conventional ones as described, for example, in A. R. Katritzky, C. W. Rees (ed.), "Comprehensive Heterocyclic Chemistry", 1st Edition, Pergamon Press 1984, in particular Vol. 3, Part 2A; D. J. Brown "The Pyrimidines", in "The Chemistry of Heterocyclic Compounds", E. C. Taylor (ed.), John Wiley & Sons Inc. NY, in particular Vol. 16+Suppl. I+II (1985) and Vol 52 (1994) and literature cited therein. The process for preparing the compounds comprises i) reacting a compound of the general formula II:

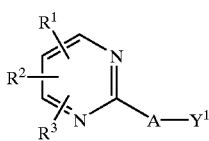

where $Y^1$ is a conventional leaving group, with a compound of the general formula III H—B—Ar;

ii) to prepare a compound of the formula I' where A is oxygen or sulfur or $NR^4$:

reacting a compound of the general formula IV:

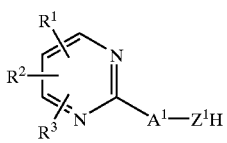

where $Z^1$ is O, S or NR , and $A^1$ is $C_0$–$C_{18}$-alkylene, with a compound of the general formula VI $Y^1$—$A^2$—B—Ar where $Y^1$ has the abovementioned meanings, and $A^2$ is $C_1$–$C_{18}$-alkylene, where $A^1$ and $A^2$ together have 1 to 18 carbon atoms, iii) to prepare a compound of the formula I' where A comprises the group COO or $CONR^4$:

reacting a compound of the general formula VII:

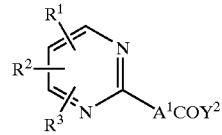

or a salt thereof, where $Y^2$ is OH, $OC_1$–$C_4$-alkyl, Cl or, together with CO, is an activated ester group, and $A^1$ has the abovementioned meanings, with a compound of the formula VIII:

$Z^1$—$A^2$—B—Ar where $A^2$ has the abovementioned meanings, and $Z^1$ is OH or $NHR^4$, iv) to prepare a compound of the formula I' where A comprises the group OCO or $NR^4CO$:

reacting a compound of the formula IV

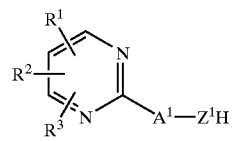

where $Z^1$ is C or $NR^4$, with a compound of the formula X:

$Y^2CO$—$A^2$—B—Ar where $A^2$, B and $Y^2$ have the abovementioned meanings, is and where $R^1$, $R^2$, $R^3$, A, B and Ar have the above-mentioned meanings.

The reactions described above generally take place in a solvent at from room temperature to the boiling point of the solvent used. Examples of solvents which can be used are ethyl acetate, tetrahydrofuran, dimethylformamide, dimethoxyethane, toluene, xylene or a ketone, such as acetone or methyl ethyl ketone.

An acid acceptor is present if required. Suitable acid acceptor s are inorganic bases such as sodium or potassium carbonate, sodium methoxide, sodium ethoxide, sodium hydride or organic bases such as triethylamine or pyridine. The latter can also serve as solvents.

The crude product is isolated in a conventional way, for example by filtration, removal of the solvent by distillation or extraction from the reaction mixture, etc. The resulting compound can be purified in a conventional way, for example by recrystallization from a solvent, chromatography or conversion into an acid addition compound.

The acid addition salts are prepared in a conventional way by mixing the free base with the appropriate acid, possibly in solution in an organic solvent, for example a lower alcohol such a methanol, ethanol or propanol, an ether such as methyl t-butyl ether, a ketone such as acetone or methyl ethyl ketone, or an ester such as ethyl acetate.

The abovementioned starting materials are disclosed in the literature or can be prepared by known processes.

To treat the abovementioned disorders, the compounds according to the invention are administered in a conventional manner orally or parenterally (subcutaneously, intravenously, intramuscularly, intraperitoneally). Administration can also take place with vapors or sprays through the nasopharyngeal space.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions which contain the compounds according to the invention. These compositions are in the usual solid or liquid pharmaceutical administration forms, for example as tablets, film-coated tablets, capsules, powders, granules, sugar-coated tablets, suppositories, solutions or sprays. The active substances can in these cases be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al., Pharmazeutische Technologie, Thieme-Verlag, Stuttgart, 1978). The administration forms obtained in this way normally contain the active substance in an amount from 1 to 99% by weight.

The following examples serve to explain the invention without limiting it.

EXAMPLE 1

4-[3-(4-{3-Trifluoromethylphenyl}piperazinyl)propylthio]pyrimidine

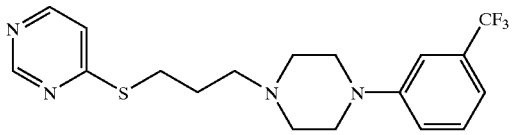

a) 1-(3-Chlorophenyl)-4-(3-trifluoromethylphenyl)piperazine 30 g (0.13 mol) of m-trifluoromethylphenylpiperazine, 23 g (0.146 mol) of 1-bromo-3-chloropropane and 15 g (0.148 mol) of triethylamine in 200 ml of THF were refluxed for 4 hours. Cooling was followed by filtration with suction and concentration. The viscous residue was taken up in ethyl acetate, washed with water, dried over $MgSO_4$ and then concentrated. The residue comprised 39 g of product as a yellowish oil (quantitative yield).

b) 4-[3-(4-{3-Trifluoromethylphenyl}piperazinyl)propylthio]pyrimidine 1.5 g (13.4 mmol) of 4-mercaptopyrimidine, 4.3 g (14 mmol) of 1-(3-chloropropyl)-4-(3-trifluoromethylphenyl)piperazine and 1.5 g (15 mmol) of triethylamine in 5 ml of DMF were stirred at 100° C. for 1 hour. The mixture was then poured into 5% strength hydrochloric acid and extracted with MTB ether. The aqueous phase was made alkaline with sodium hydroxide solution and then extracted with ethyl acetate, and the organic phase was dried over $MgSO_4$ and concentrated. The residue was purified by chromatography (mobile phase: $CH_2Cl_2/CH_3OH=98/2$). 3.0 g of product were obtained as a yellowish oil (=59% yield).

H-NMR [δ, ppm]: 1.95 (2H); 2.55 (2H); 2.65 (4H); 3.25 (6H); 7.06 (3H); 7.15 (1H); 7.35 (1H); 8.33 (1H); 8.9 (1H).

EXAMPLE 2

2-(5-(4-{3-Trifluoromethylphenyl}piperazinyl)pentylmercaptolpyrimidine

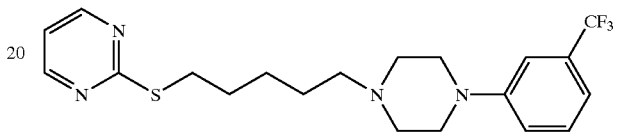

a) 2-(5-Chloropentylmercapto)pyrimidine 2.8 g (25=mol) of 2-mercaptopyrimidine, 4.64 g (25 mmol) of 1-bromo-5-chloropentane and 2.58 g (25.5 mmol) of triethylamine in 100 ml of THF were refluxed for 4 hours. After cooling, filtration with suction and concentration, the residue was purified by chromatography (mobile phase: cyclohexane/ethyl acetate=92/8). 2.8 g of product were obtained (=52% yield).

b) 2-[5-(4-{3-Trifluoromethylphenyl}piperazinyl)pentylmercapto]pyrimidine 2.8 g (12.9 mmol) of 2-(5-chloropentylmercapto)pyrimidine, 3.27 g (14.2 mmol) of m-trifluoromethylphenylpiperazine and 1.44 g (14.2 mmol) of triethylamine in 5 ml of DMF were stirred at 90° C. for 1 hour. The mixture was then poured onto water and extracted three times with $CH_2Cl_2$, and the extracts were dried over $MgSO_4$ and concentrated. The residue was mixed with methyl t-butyl ether and filtered with suction, and the mother liquor was concentrated. Purification by chromatography (mobile phase: $CH_2Cl_2/CH_3OH=97/3$) resulted in 4.0 g of product as oil (=75% yield).

H-NMR [δ, ppm]: 1.54 (4H); 1.78 (2H); 2.4 (2H); 2.6 (4H); 3.18 (2H); 3.23 (4H); 6.95 (1H); 7.01 (3H); 7.1 (3H); 7.33 (1H); 8.5 (1H).

The compounds indicated in Table 1 below were prepared in a similar way:

TABLE 1

| No. | Example | physical data, H-NMR [δ, ppm] Melting point [° C.] |
|---|---|---|
| 3 | ![structure] | 2.0(2H); 2.5(3H); 2.55(2H); 2.63(4H); 3.23(6H); 6.8(1H); 7.1(3H); 7.35(1H); 8.36(1H) |

TABLE 1-continued

| No. | Example | physical data, H-NMR [δ, ppm] Melting point [° C.] |
|---|---|---|
| 4 | | 1.8(2H); 2.45(6H); 3.1(2H); 3.2(4H); 5.0(1H); 7.05(1H); 7.15(1H); 7.2(1H); 7.4(1H) |
| 5 | | 1.5(4H); 1.75(2H); 2.4(2H); 2.6(4H); 3.2(2H); 3.25(6H); 6.22(1H); 7.1(3H); 7.35(1H); 7.85(1H); 11.3(1H) |
| 6 | | 129–130 |
| 7 | | 0.97(3H); 2.0–2.3(3H); 2.5(4H); 2.8(1H); 3.2(6H); 6.1(1H); 6.85(2H); 7.07(1H); 7.2(1H); 7.4(1H); 7.9(1H) |
| 8 | | 2.0(2H); 2.4(6H); 2.55(2H); 2.43(4H); 3.23(6H); 6.7(1H); 7.1(3H); 7.36(1H) |
| 9 | x HCl | 2.0(2H); 2.62(2H); 2.7(4H); 3.2(2H); 3.28(4H); 5.95(1H); 6.95(1H); 7.1(3H); 7.35(1H); 8.55(2H); |
| 10 | | 1.95(2H); 2.5(2H); 2.6(4H); 3.15(2H); 3.27(4H); 4.87(2H); 6.15(1H); 7.1(3H); 7.35(1H); 8.06(1H) |
| 11 | | 1.75(4H); 2.45(2H); 2.62(4H); 3.22(6H); 6.98(1H); 7.1(3H); 7.35(1H); 8.5(2H) |
| 12 | | 1.98(2H); 2.55(2H); 2.65(4H); 3.25(6H); 6.21(1H); 7.1(3H); 7.35(1H); 7.85(1H) |

TABLE 1-continued

| No. | Example | physical data, H-NMR [δ, ppm] Melting point [° C.] |
|---|---|---|
| 13 | (structure) x 2HCl | 131–132 |
| 14 | (structure) | 2.6(4H); 3.03(2H); 3.23(4H); 3.78(2H); 4.85(2H); 5.8(2H) 6.13(1H); 7.06(3H); 7.33(1H); 8.05(1H) |
| 15 | (structure) x HCl | 232–234 |
| 16 | (structure) x HCl | 188–190 |
| 17 | (structure) | 1.26(6H); 2.0(2H); 2.59 (2H); 2.66(4H); 2.88(1H); 3.2(6H); 6.2(1H); 6.78 (3H); 7.2(1H); 7.8(1H) |
| 18 | (structure) | 70–83 |
| 19 | (structure) | 2.0(2H); 2.65(4H); 2.8(2H); 3.28(4H); 6.15(1H); 6.2(1H); 7.5(3H); 7.63(1H); 7.85(1H) |
| 20 | (structure) | 1.5(1H); 2(7H); 2.58(2H); 3.05(3H); 3.2(2H); 6.18(1H); 7.45(4H); 7.8(1H) |

TABLE 1-continued

| No. | Example | physical data, H-NMR [δ, ppm] Melting point [° C.] |
|---|---|---|
| 21 | | 151–153 |
| 22 | | 180–186 |
| 23 | | 170–174 |
| 24 | | 1.45(6H); 1.75(2H); 2.4(2H); 2.6(4H); 3.2(2H); 3.25(4H); 6.2(1H); 7.1(3H); 7.32(1H); 7.88(1H) |
| 25 | | 1.8–2.2(8H); 2.6(3H); 3.1(2H); 3.25(2H); 6.2(1H); 7.45(4H); 7.8(1H) |
| 26 | | 144–156 |
| 27 | | 200–205 |
| 28 | | 165–171 |
| 29 | | 169–172 |

TABLE 1-continued

| No. | Example | physical data, H-NMR [δ, ppm] Melting point [° C.] |
|---|---|---|
| 30 | | 161–165 |
| 31 | | 174–176 |
| 32 | | 60–71 |
| 33 | | 2.0(2H); 2.6(6H); 3.25(6H); 6.2(1H); 6.85(1H); 6.95(1H); 7.15(1H); 7.25(1H); 7.85(1H) |
| 34 | | 2.0(2H); 2.56(2H); 2.65(4H); 3.25(6H); 6.18(1H); 6.6(1H); 7.0(2H); 7.04(1H); 7.33(1H); 7.82(1H) |
| 35 | | 1.15(6H); 1.82(2H); 2.4(2H); 2.5(8H); 3.1(6H); 6.1(1H); 6.5(1H); 6.58(2H); 7.85(1H) |
| 36 | | 1.3(18H); 2.0(2H); 2.55(2H); 2.65(4H); 3.25(6H); 6.2(1H); 6.8(2H); 7.0(1H); 7.85(1H) |

TABLE 1-continued
| No. | Example | physical data, H-NMR [δ, ppm] Melting point [° C.] |
|---|---|---|
| 37 | 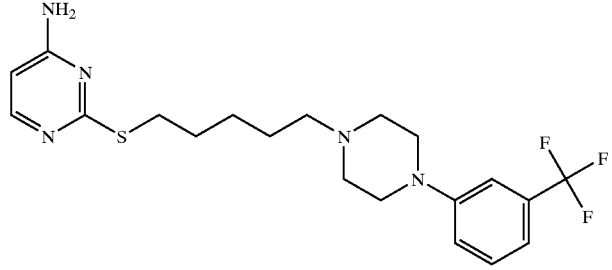 | |
| 38 | 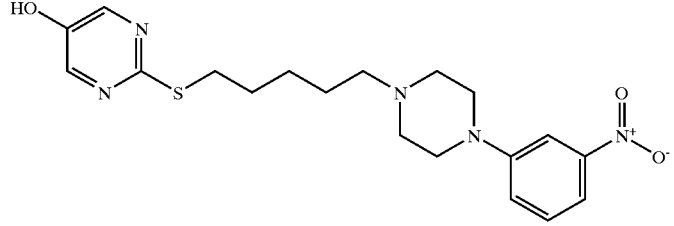 | 151–153° C. |
| 39 | 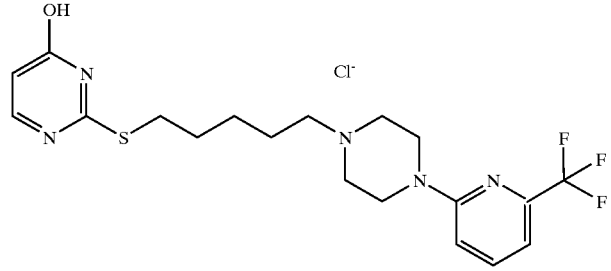 | 170–175° C. Hydrochloride |
| 40 | 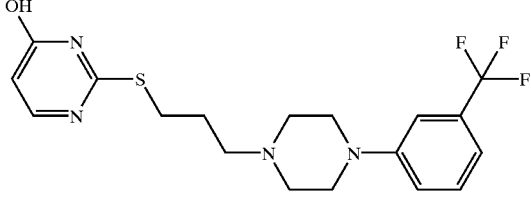 | 189–190° C. Hydrochloride |
| 41 | 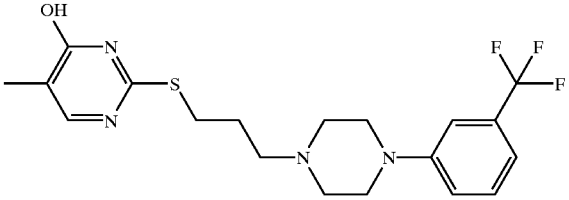 | 158–160° C. Hydrochloride |

TABLE 1-continued

| No. | Example | physical data, H-NMR [δ, ppm] Melting point [° C.] |
|---|---|---|
| 42 | | 132–134° C. |
| 43 | | |
| 44 | | 118–125° C. |
| 45 | | 163–166° C. |
| 46 | | 109–114° C. |
| 47 | | 201–203° C. |

TABLE 1-continued

| No. | Example | physical data, H-NMR [δ, ppm] Melting point [° C.] |
|---|---|---|
| 48 | (structure: 2-((3-(4-(2-tert-butyl-6-(trifluoromethyl)pyrimidin-4-yl)piperazin-1-yl)propyl)thio)pyrimidin-4-ol) | 138–140° C. |
| 49 | (structure: 2-((3-(4-(3-nitropyridin-4-yl)piperazin-1-yl)propyl)thio)pyrimidin-4-ol) | 138–140° C. |
| 50 | (structure: 2-((3-(4-(6-chloro-4-(trifluoromethyl)pyridin-2-yl)piperazin-1-yl)propyl)thio)pyrimidin-4-ol) · fumarate | 77–80° C.<br>290–295° C.<br>(Fumarate) |
| 51 | (structure: 2-((3-(4-(3,5-di-tert-butylphenyl)piperazin-1-yl)propyl)thio)pyrimidin-4-amine) · fumarate | 128–130° C.<br>(Fumarate) |

TABLE 1-continued

| No. | Example | physical data, H-NMR [δ, ppm] Melting point [°C.] |
|---|---|---|
| 53 | | 158–160° C. (Fumarate) |
| 54 | | 138–141° C. (Fumarate) |
| 55 | | 55–60° C. |
| 56 | | 62–70° C. |

TABLE 1-continued

| No. | Example | physical data, H-NMR [δ, ppm] Melting point [° C.] |
|---|---|---|
| 57 | | 70–73° C. |
| 58 | | 127–134° C. Hydrochloride |
| 59 | | 85–90° C. |
| 60 | | 204–210° C. |
| 61 | | 137–191° C. |

The compounds mentioned in Tables 2–6 below can obtained in a similar manner.

TABLE 2

| Example No. | R1 | R2 | R3 | R6 | R7 | R8 | R9 | R10 | X–Y | A | B |
|---|---|---|---|---|---|---|---|---|---|---|---|
| 62 | H | H | OH | H | tBut | H | Me | H | CH$_2$—N | —CH$_2$— | —(CH$_2$)$_3$— |
| 63 | H | H | OH | H | tBut | H | Ph | H | CH=C | S | —(CH$_2$)$_3$— |
| 64 | Me | H | OH | H | tBut | H | 1-Pyrrolyl | H | CH=C | S | —(CH$_2$)$_3$— |
| 65 | H | H | NH$_2$ | H | iProp | H | 2-Napht | H | CH=C | S | —(CH$_2$)$_3$— |
| 66 | H | Me | OH | H | Et | H | tBut | H | CH$_2$—N | —CH$_2$— | —(CH$_2$)$_3$— |
| 67 | H | H | OH | OMe | tBut | H | H | H | CH=C | S | —(CH$_2$)$_3$— |
| 68 | H | H | NH$_2$ | OMe | CF$_3$ | H | H | H | CH=C | S | —(CH$_2$)$_3$— |
| 69 | H | H | OH | H | CF$_3$ | H | tBut | H | CH$_2$—N | —CH$_2$— | —(CH$_2$)$_3$— |
| 70 | H | H | NHMe | OiProp | iProp | H | H | H | CH$_2$—N | O | —(CH$_2$)$_4$— |
| 71 | Me | H | OH | H | H | CN | tBut | H | CH$_2$—N | —CH$_2$— | —(CH$_2$)$_3$— |
| 72 | H | H | OH | H | H | F | tBut | H | CH=C | S | —(CH$_2$)$_3$— |
| 73 | H | Me | NH$_2$ | H | H | Cl | iProp | H | CH$_2$—N | —CH$_2$— | —(CH$_2$)$_3$— |
| 74 | H | H | NHMe | H | tBut | H | H | OMe | CH=C | S | —(CH$_2$)$_3$— |
| 75 | H | H | OH | H | iProp | H | H | OMe | CH$_2$—N | —CH$_2$— | —(CH$_2$)$_4$— |
| 76 | H | H | OH | OMe | tBut | H | tBut | H | CH=C | S | —(CH$_2$)$_3$— |
| 77 | H | H | OH | OMe | tBut | H | CF$_3$ | H | CH$_2$—N | —CH$_2$— | —(CH$_2$)$_3$— |
| 78 | Me | H | OH | OMe | CF$_3$ | H | tBut | H | CH$_2$—N | O | —(CH$_2$)$_5$— |
| 79 | H | H | NH$_2$ | H | nProp | CN | tBut | H | CH$_2$—N | —CH$_2$— | —(CH$_2$)$_3$— |
| 80 | H | Me | OH | H | CF$_3$ | CN | iProp | H | CH=C | S | —(CH$_2$)$_3$— |
| 81 | H | H | OH | H | Ph | C=CH | tBut | H | CH$_2$—N | —CH$_2$— | —(CH$_2$)$_3$— |
| 82 | H | H | NH$_2$ | OMe | tBut | CN | H | H | CH=C | S | —(CH$_2$)$_3$— |
| 83 | H | H | NHMe | H | tBut | CN | CF$_3$ | OMe | CH$_2$—N | —CH$_2$— | —(CH$_2$)$_5$— |
| 84 | H | H | OH | OMe | nProp | F | tBut | H | CH$_2$—N | —CH$_2$— | —(CH$_2$)$_4$— |
| 85 | H | H | OH | H | Ph | CN | tBut | Me | CH=C | S | —(CH$_2$)$_3$— |
| 86 | H | H | OH | OMe | tBut | F | H | H | CH$_2$—N | —CH$_2$— | —(CH$_2$)$_3$— |
| 87 | H | H | OH | H | tBut | H | Me | H | CH$_2$—N | —CH$_2$— | —CH$_2$—CH=CH—CH$_2$— |
| 88 | H | H | OH | H | tBut | H | Ph | H | CH=C | S | —CH$_2$—CH=CH—CH$_2$— |
| 89 | Me | H | OH | H | tBut | H | 1-Pyrrolyl | H | CH=C | S | —CH$_2$—CH=CH—CH$_2$— |
| 90 | H | H | NH$_2$ | H | iProp | H | 2-Napht | H | CH=C | S | —CH$_2$—C(CH$_3$)=CH—CH$_2$— |
| 91 | H | Me | OH | H | Et | H | tBut | H | CH$_2$—N | —CH$_2$— | —CH$_2$—C(CH$_3$)=CH—CH$_2$— |
| 92 | H | H | OH | OMe | tBut | H | H | H | CH=C | S | —CH$_2$—C(CH$_3$)=CH—CH$_2$— |
| 93 | H | H | NH$_2$ | OMe | CF$_3$ | H | H | H | CH=C | S | —CH$_2$—C(CH$_3$)=CH—CH$_2$— |
| 94 | H | H | OH | H | CF$_3$ | H | tBut | H | CH$_2$—N | —CH$_2$— | —CH$_2$—CH=CH—CH$_2$— |
| 95 | H | H | NHMe | OiProp | iProp | H | H | H | CH$_2$—N | O | —CH$_2$—CH=CH—CH$_2$— |
| 96 | Me | H | OH | H | H | CN | tBut | H | CH$_2$—N | —CH$_2$— | —CH$_2$—CH=CH—CH$_2$— |
| 97 | H | H | OH | H | H | F | tBut | H | CH=C | S | —CH$_2$—C(CH$_3$)=CH—CH$_2$— |
| 98 | H | Me | NH$_2$ | H | H | Cl | iProp | H | CH$_2$—N | —CH$_2$— | —CH$_2$—C(CH$_3$)=CH—CH$_2$— |
| 99 | H | H | NHMe | H | tBut | H | H | OMe | CH=C | S | —CH$_2$—C(CH$_3$)=CH—CH$_2$— |
| 100 | H | H | OH | H | iProp | H | H | OMe | CH$_2$—N | —CH$_2$— | —CH$_2$—C(CH$_3$)=CH—CH$_2$— |
| 101 | H | H | OH | OMe | tBut | H | tBut | H | CH=C | S | —CH$_2$—CH=CH—CH$_2$— |
| 102 | H | H | OH | OMe | tBut | H | CF$_3$ | H | CH$_2$—N | —CH$_2$— | —CH$_2$—CH=CH—CH$_2$— |
| 103 | Me | H | OH | OMe | CF$_3$ | H | tBut | H | CH$_2$—N | O | —CH$_2$—CH=CH—CH$_2$— |
| 104 | H | H | NH$_2$ | H | nProp | CN | tBut | H | CH$_2$—N | —CH$_2$— | —CH$_2$—C(CH$_3$)=CH—CH$_2$— |
| 105 | H | Me | OH | H | CF$_3$ | CN | iProp | H | CH=C | S | —CH$_2$—C(CH$_3$)=CH—CH$_2$— |
| 106 | H | H | OH | H | Ph | C=CH | tBut | H | CH$_2$—N | —CH$_2$— | —CH$_2$—C(CH$_3$)=CH—CH$_2$— |
| 107 | H | H | NH$_2$ | OMe | tBut | CN | H | H | CH=C | S | —CH$_2$—C(CH$_3$)=CH—CH$_2$— |
| 108 | H | H | NHMe | H | tBut | CN | CF$_3$ | OMe | CH$_2$—N | —CH$_2$— | —CH$_2$—CH=CH—CH$_2$— |
| 109 | H | H | OH | OMe | nProp | F | tBut | H | CH$_2$—N | —CH$_2$— | —CH$_2$—C(CH$_3$)=CH—CH$_2$— |
| 110 | H | H | OH | H | Ph | CN | tBut | Me | CH=C | S | —CH$_2$—C(CH$_3$)=CH$_{13}$CH$_2$— |
| 111 | H | H | OH | OMe | tBut | F | H | H | CH$_2$—N | —CH$_2$— | —CH$_2$—CH=CH—CH$_2$— |

TABLE 3

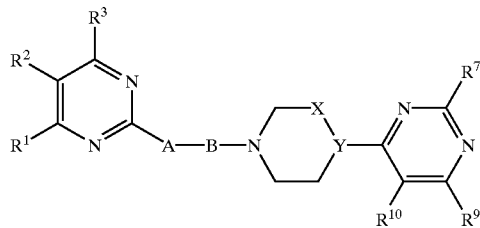

| Example No. | R1 | R2 | R3 | R7 | R9 | R10 | X–Y | A | B |
|---|---|---|---|---|---|---|---|---|---|
| 112 | H | H | OH | tBut | Ph | H | $CH_2$—N | —$CH_2$— | —$(CH_2)_3$— |
| 113 | H | H | OH | tBut | 2-Napht | H | $CH_2$—N | S | —$(CH_2)_3$— |
| 114 | Me | H | OH | tBut | 1-Pyrrolyl | H | $CH_2$—N | S | —$CH_2$—CH=CH—$CH_2$— |
| 115 | H | H | $NH_2$ | tBut | cHex | H | CH=C | —$CH_2$— | —$CH_2$—C($CH_3$)=CH—$CH_2$— |
| 116 | H | H | OH | tBut | nHex | H | $CH_2$—N | S | —$(CH_2)_3$— |
| 117 | H | H | OH | tBut | H | OMe | $CH_2$—N | —$CH_2$— | —$CH_2$—C($CH_3$)=CH—$CH_2$— |
| 118 | H | Me | OH | iProp | H | OMe | $CH_2$—N | S | —$CH_2$—CH=CH—$CH_2$— |
| 119 | H | H | $NH_2$ | H | $CH_3$ | OMe | CH=C | NH | —$(CH_2)_3$— |
| 120 | H | H | OH | H | iProp | OMe | $CH_2$—N | O | —$(CH_2)_3$— |
| 121 | H | H | OH | tBut | H | $CH_3$ | $CH_2$—N | S | —$CH_2$—C($CH_3$)=CH—$CH_2$— |
| 122 | H | H | OH | tBut | tBut | OMe | $CH_2$—N | S | —$(CH_2)_3$— |
| 123 | Me | H | OH | tBut | iProp | OMe | $CH_2$—N | S | —$CH_2$—CH=CH—$CH_2$— |
| 124 | H | H | $NH_2$ | Ph | tBut | Cl | CH=C | —$CH_2$— | —$CH_2$—C($CH_3$)=CH—$CH_2$— |
| 125 | H | H | OH | 2-Napht | tBut | Me | $CH_2$—N | S | —$(CH_2)_3$— |
| 126 | H | H | OH | tBut | $CF_3$ | OMe | $CH_2$—N | —$CH_2$— | —$CH_2$—C($CH_3$)=CH—$CH_2$— |

TABLE 4

| Example No. | R1 | R2 | R3 | R7 | R8 | R9 | R10 | X–Y | A | B |
|---|---|---|---|---|---|---|---|---|---|---|
| 127 | H | H | OH | tBut | H | tBut | H | $CH_2$—N | S | —$(CH_2)_3$— |
| 128 | H | H | OH | tBut | CN | H | H | $CH_2$—N | S | —$(CH_2)_3$— |
| 129 | Me | H | OH | tBut | H | H | OMe | $CH_2$—N | NH | —$CH_2$—CH=CH—$CH_2$— |
| 130 | H | H | OH | H | CN | tBu | H | CH=C | —$CH_2$— | —$CH_2$—C($CH_3$)=CH—$CH_2$— |
| 131 | H | H | $NH_2$ | $CF_3$ | H | tBut | H | $CH_2$—N | S | —$(CH_2)_3$— |
| 132 | H | H | OH | nProp | H | iProp | H | CH=C | —$CH_2$— | —$(CH_2)_3$— |
| 133 | H | Me | OH | H | H | iProp | OMe | CH=C | S | —$(CH_2)_3$— |
| 134 | H | H | OH | tBut | H | tBut | H | $CH_2$—N | NH | —$CH_2$—CH=CH—$CH_2$— |
| 135 | H | H | OH | tBut | CN | H | H | $CH_2$—N | S | —$(CH_2)_4$— |
| 136 | H | H | $NH_2$ | tBut | H | H | OMe | $CH_2$—N | O | —$(CH_2)_3$— |
| 137 | Me | H | OH | H | CN | tBu | H | CH=C | S | —$CH_2$—C($CH_3$)=CH—$CH_2$— |
| 138 | H | H | OH | $CF_3$ | H | tBut | H | $CH_2$—N | —$CH_2$— | —$(CH_2)_3$— |
| 139 | H | H | OH | nProp | H | iProp | H | $CH_2$—N | S | —$(CH_2)_3$— |
| 140 | H | H | NHMe | H | H | iProp | OMe | $CH_2$—N | S | —$(CH_2)_3$— |
| 141 | H | H | OH | nProp | CN | tBut | H | $CH_2$—N | S | —$(CH_2)_4$— |
| 142 | H | H | OH | $CF_3$ | CN | iProp | H | $CH_2$—N | S | —$(CH_2)_3$— |
| 143 | Me | H | OH | Ph | C=CH | tBut | H | $CH_2$—N | NH | —$CH_2$—CH=CH—$CH_2$— |
| 144 | H | H | OH | tBut | CN | tBut | H | CH=C | —$CH_2$— | —$CH_2$—C($CH_3$)=CH—$CH_2$— |
| 145 | H | H | $NH_2$ | tBut | H | nProp | OMe | $CH_2$—N | S | —$(CH_2)_3$— |
| 146 | H | H | OH | Ph | H | tBut | OMe | CH=C | —$CH_2$— | —$(CH_2)_5$— |
| 147 | H | Me | OH | $CF_3$ | H | tBut | OMe | CH=C | S | —$(CH_2)_3$— |
| 148 | H | H | OH | tBut | F | H | Me | $CH_2$—N | NH | —$CH_2$—CH=CH—$CH_2$— |
| 149 | H | H | OH | nProp | CN | tBut | Me | $CH_2$—N | S | —$CH_2$—CH=CH—$CH_2$— |
| 150 | H | H | $NH_2$ | nProp | C=CH | tBut | OMe | CH=C | —$CH_2$— | —$CH_2$—C($CH_3$)=CH—$CH_2$— |
| 151 | H | H | OH | tBut | CN | H | OMe | $CH_2$—N | S | —$(CH_2)_4$— |

TABLE 5

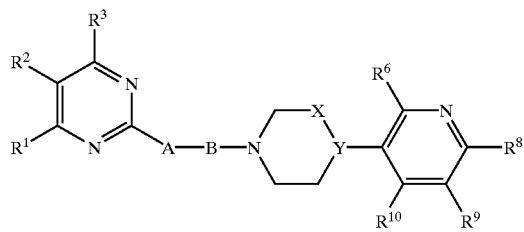

| Example No. | R1 | R2 | R3 | R6 | R8 | R9 | R10 | X—Y | A | B |
|---|---|---|---|---|---|---|---|---|---|---|
| 152 | H | H | OH | OMe | H | tBut | H | $CH_2$—N | S | —$(CH_2)_3$— |
| 153 | H | H | OH | OMe | H | $CF_3$ | H | $CH_2$—N | S | —$(CH_2)_3$— |
| 154 | Me | H | OH | OMe | H | tBut | H | $CH_2$—N | NH | —$CH_2$—CH=CH—$CH_2$— |
| 155 | H | H | OH | H | CN | tBut | H | CH=C | —$CH_2$— | —$CH_2$—C($CH_3$)=CH—$CH_2$— |
| 156 | H | H | $NH_2$ | H | F | tBut | H | $CH_2$—N | S | —$(CH_2)_3$— |
| 157 | H | H | OH | Me | Cl | iProp | H | CH=C | S | —$(CH_2)_3$— |
| 158 | H | Me | OH | H | H | iProp | OMe | CH=C | S | —$(CH_2)_3$— |
| 159 | H | H | OH | H | H | tBut | OMe | $CH_2$—N | NH | —$CH_2$—CH=CH—$CH_2$— |
| 160 | H | H | OH | CN | H | $CF_3$ | H | $CH_2$—N | S | —$(CH_2)_4$— |
| 161 | H | H | $NH_2$ | H | CN | H | OMe | $CH_2$—N | O | —$(CH_2)_3$— |
| 162 | Me | H | OH | H | H | tBu | OEt | CH=C | S | —$CH_2$—C($CH_3$)=CH—$CH_2$— |
| 163 | H | H | OH | H | CN | tBut | H | $CH_2$—N | —$CH_2$— | —$(CH_2)_3$— |
| 164 | H | H | OH | Me | H | iProp | H | $CH_2$—N | S | —$(CH_2)_3$— |
| 165 | H | H | NHMe | OMe | H | iProp | H | $CH_2$—N | S | —$(CH_2)_3$— |
| 166 | H | H | OH | OMe | CN | tBut | H | $CH_2$—N | S | —$(CH_2)_3$— |
| 167 | H | H | OH | OMe | Me | tBut | H | $CH_2$—N | S | —$(CH_2)_3$— |
| 168 | Me | H | OH | H | CN | tBut | OMe | $CH_2$—N | NH | —$CH_2$—CH=CH—$CH_2$— |
| 169 | H | H | OH | Me | H | tBut | OMe | CH=C | —$CH_2$— | —$CH_2$—C($CH_3$)=CH—$CH_2$— |
| 170 | H | H | $NH_2$ | H | Cl | $CF_3$ | Me | $CH_2$—N | S | —$(CH_2)_3$— |
| 171 | H | H | OH | OMe | CN | tBut | Me | CH=C | —$CH_2$— | —$(CH_2)_3$— |
| 172 | H | Me | OH | Me | Me | iProp | Me | CH=C | S | —$(CH_2)_3$— |

TABLE 6

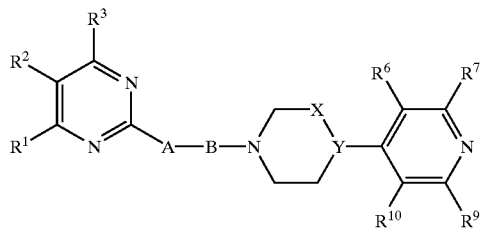

| Example No. | R1 | R2 | R3 | R6 | R7 | R9 | R10 | X—Y | A | B |
|---|---|---|---|---|---|---|---|---|---|---|
| 173 | H | H | OH | H | tBut | tBut | H | $CH_2$—N | S | —$(CH_2)_3$— |
| 174 | H | H | OH | H | tBut | Ph | H | $CH_2$—N | S | —$(CH_2)_3$— |
| 175 | Me | H | OH | H | tBut | 1-Pyrrolyl | H | $CH_2$—N | NH | —$CH_2$—CH=CH—$CH_2$— |
| 176 | H | H | OH | H | nPropyl | tBut | H | CH=C | —$CH_2$— | —$CH_2$—C($CH_3$)=CH—$CH_2$— |
| 177 | H | H | $NH_2$ | H | $CF_3$ | tBut | H | $CH_2$—N | S | —$(CH_2)_3$— |
| 178 | H | H | OH | H | 2-Napth | tBut | H | CH=C | —$CH_2$— | —$(CH_2)_3$— |
| 179 | H | Me | OH | OMe | tBut | H | H | CH=C | S | —$(CH_2)_3$— |
| 180 | H | H | OH | OMe | iProp | H | H | $CH_2$—N | NH | —$CH_2$—CH=CH—$CH_2$— |
| 181 | H | H | OH | OMe | H | $CF_3$ | H | $CH_2$—N | S | —$(CH_2)_4$— |
| 182 | H | H | $NH_2$ | H | tBut | H | OMe | $CH_2$—N | O | —$(CH_2)_3$— |
| 183 | Me | H | OH | H | iProp | H | Me | CH=C | S | —$CH_2$—C($CH_3$)=CH—$CH_2$— |
| 184 | H | H | OH | CN | tBut | H | H | $CH_2$—N | —$CH_2$— | —$(CH_2)_3$— |
| 185 | H | H | OH | H | H | $CF_3$ | Me | $CH_2$—N | S | —$(CH_2)_3$— |
| 186 | H | H | NHMe | H | nProp | tBut | H | $CH_2$—N | S | —$(CH_2)_3$— |
| 187 | H | H | OH | OMe | tBut | iProp | H | $CH_2$—N | S | —$(CH_2)_4$— |
| 188 | H | H | OH | OMe | $CF_3$ | tBut | H | $CH_2$—N | NH | —$CH_2$—CH=CH—$CH_2$— |
| 189 | Me | H | OH | Me | tBut | nProp | H | CH=C | —$CH_2$— | —$CH_2$—C($CH_3$)=CH—$CH_2$— |
| 190 | H | H | OH | Me | tBut | H | OMe | $CH_2$—N | S | —$(CH_2)_5$— |
| 191 | H | H | $NH_2$ | OMe | tBut | tBut | OMe | CH=C | —$CH_2$— | —$(CH_2)_3$— |
| 192 | H | H | OH | Me | $CF_3$ | tBut | OMe | CH=C | S | —$(CH_2)_3$— |

Examples of Pharmaceutical Forms

A) Tablets
Tablets of the followwing composition are compressed in a tabletting machine ina conventional manner

| | |
|---|---|
| 40 mg | of substance of Example 1 |
| 120 mg | of corn starch |
| 13.5 mg | of gelatin |
| 45 mg | of lactose |
| 2.25 mg | of Aerosil ™ (chemically pure silica in submicroscopically fine dispersion) |
| 6.75 mg | of potato starch (as 6% strength paste) |

B) Sugar-coated tablets

| | |
|---|---|
| 20 mg | of substance of Example 4 |
| 60 mg | of core composition |
| 70 mg | of sugar-coating composition |

The core composition comprises 9 parts of corn starch, 3 parts of lactose and 1 part of vinylpyrrolidone/vinyl acetate 60:40 copolymer. The sugar-coating composition comprises 5 parts of sucrose, 2 parts of corn starch, 2 parts of calcium carbonate and 1 part of talc. The sugar-coated tablets produced in this way are subsequently provided with an enteric coating.

Biolocrical Investigations—Receptor-binding Studies

1) $D_3$ Binding Assay

Cloned human $D_3$ receptor-expressing CCL 1.3 mouse fibroblasts obtained from Res. Biochemicals Internat. One Strathmore Rd., Natick, Mass. 01760-2418 USA, were used for the binding studies.

Cell Preparation

The $D_3$-expressing cells were grown in RPMI-1640 containing 10% fetal calf serum (GIBCO No. 041-32400 N); 100 U/ml penicillin and 0.2% streptomycin (GIBCO BRL, Gaithersburg, Md., USA). After 48 h, the cells were washed with PBS and incubated with 0.05% trypsin-containing PBS for 5 min. Neutralization with medium was then carried out, and the cells were collected by centrifugation at 300×g. To lyze the cells, the pellet was briefly washed with lysis buffer (5 mM tris-HCl, pH 7.4, with 10% glycerol) and then incubated in a concentration of $10^7$ cells/ml of lysis buffer at 4° C. for 30 min. The cells were centrifuged at 200×g for 10 min and the pellet was stored in liquid nitrogen.

Binding Assays

For the $D_3$ receptor-binding assay, the membranes were suspended in incubation buffer (50 mM tris-HCl, pH 7.4, with 120 mM NaCl, 5 mM KCl, 2 mM $CaCl_2$, 2 mM $MgCl_2$, 10 μM quinolinol, 0.1% ascorbic acid and 0.1% BSA) in a concentration of about $10^6$ cells/250 μl of assay mixture and incubated at 30° C. with 0.1 nM $^{125}$iodosulpiride in the presence and absence of test substance. The non-specific binding was determined using $10^{-6}$ M spiperone.

After 60 min, the free and the bound radioligand was separated by filtration through GF/B glass fiber filters (Whatman, England) on a Skatron cell collector (Skatron, Lier, Norway), and the filters were washed with ice-cold tris-HCl buffer, pH 7.4. The radioactivity collected on the filters was quantified using a Packard 2200 CA liquid scintillation counter.

The $K_i$ values were determined by non-linear regression analysis using the LIGAND program.

2) $D_2$ Binding Assay

Membrane Preparation a) Nucleus Caudatus (Bovine)

Nucleus caudatus was removed from bovine brain and washed in ice-cold 0.32 M sucrose solution. After determination of the weight, the material was comminuted and homogenized in 5–10 volumes of sucrose solution using a Potter-Evehjem [sic] homogenizer (500 rpm). The homogenate was centrifuged at 3,000×g for 15 minutes (4° C.), and the resulting supernatant was subjected to another 15-minute centrifugation at 40,000×g. The residue was then washed twice, by resuspension and centrifugation, with 50 mM tris-HCl, pH 7.4. The membranes were stored in liquid $N_2$ until used.

b) Striatum (Rat)

Striati from Sprague-Dawley rats were washed in ice-cold 0.32 M sucrose solution. After determination of the weight, the parts of the brain were homogenized in 5–10 volumes of sucrose solution using a Potter-Elvehjem homogenizer (500 rpm). The homogenate was centrifuged at 40,000×g for 10 minutes (4° C.), and then the residue was washed several times, by resuspension and centrifugation, with 50 mM tris-HCl, 0.1 mM EDTA and 0.01% ascorbic acid (pH 7.4). The washed residue was resuspended in the abovementioned buffer and incubated at 37° C. for 20 minutes (to break down the endogenous dopamine). The membranes were then washed twice with buffer and portions were frozen in liquid nitrogen. The membrane prepration [sic] was stable for a maximum of 1 week.

Binding Assay a) $^3$H-Spiperone ($D_{2low}$)

Nucleus caudatus membranes were taken up in incubation buffer (mM: tris-HCl 50, NaCl 120, KCl 5, $MgCl_2$ 1, $CaCl_2$ 2, pH 7.4). Various mixtures, each of 1 ml, were prepared:

Total binding: 400 μg of membranes+0.2 mmol/l $^3$H-spiperone (Du Pont de Nemours, NET-565).

Non-specific binding: as mixtures for total binding+10 μM (+)-butaclamol.

Test substance: as mixtures for total binding+increasing concentrations of test substance.

After incubation at 25° C. for 60 minutes, the mixtures were filtered through GF/B glass fiber filters (Whatman, England) on a Skatron cell selector (from Zinsser, Frankfurt), and the filters were washed with ice-cold 50 mM tris-HCl buffer, pH 7.4. The radioactivity collected on the filters was quantified using a Packard 2200 CA liquid scintillation counter.

The $K_i$ values were determined by non-linear regression analysis using the LIGAND program or by conversion of the $IC_{50}$ values using the formula of Cheng and Prusoff.

b) $^3$H-ADTN ($D_{2high}$)

Striatum membranes were taken up in incubation buffer (50 mM tris-HCl, pH 7.4, 1 mM $MnCl_2$ and 0.1% ascorbic acid).

Various mixtures, each of 1 ml, were prepared.

Total binding: 300 μg wet weight+1 nM $^3$H-ADTN (Du Pont de Nemours, customer synthesis)+100 nM SCH 23390 (occupation of D1 receptors).

Non-specific binding: as mixtures for total binding+50 nM spiperone.

Test substance: as mixtures for total binding+increasing concentrations of test substance.

After incubation at 25° C. for 60 minutes, the mixtures were filtered through GF/B glass fiber filters (Whatman, England) on a Skatron cell selector (from Zinsser, Frankfurt), and the filters were washed with ice-cold 50 mM tris-HCl buffer, pH 7.4. The radioactivity collected on the filters was quantified using a Packard 2200 CA liquid scintillation counter.

The evaluation took place as under a).

In these assays, the compounds according to the invention show very good affinities and high selectivities for the $D_3$ receptor. The results for representative compounds are compiled in the following Table 7.

TABLE 7

| Example No. | Receptor binding $D_3$ $^{125}$I-sulpiride $K_i$ [nM] | $D_2$ $^3$H-spiperone $K_i$ [nM] | Selectivity $K_i D_2/K_i D_2$ |
|---|---|---|---|
| 12 | 4.2 | 357 | 85 |
| 13 | 2.3 | 142 | 61 |
| 17 | 2.8 | 200 | 71 |
| 19 | 3.0 | 175 | 58 |
| 48 | 4.0 | 480 | 120 |

We claim:

1. A pyrimidine compound of formula I

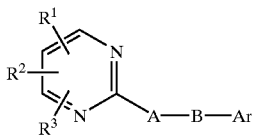

(I)

wherein

A is $C_2-C_{15}$-alkylene which is interrupted by, or which is bonded to the pyrimidine ring through, a radical $NR^4$, B is

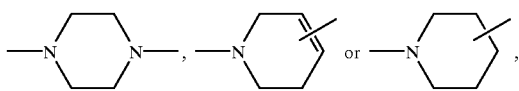

$R^1$, $R^2$, $R^3$ are, independently of one another, H, halogen, $OR^4$, $NR^4R^5$, $SR^4$ $CF_3$, CN, $CO_2R^4$ or $C_1-C_8$-alkyl which is unsubstituted or substituted by OH, $OC_1-C_8$-alkyl or halogen, $R^4$ is H, $C_1-C_8$-alkyl which is unsubstituted or substituted by OH, $OC_1-C_8$-alkyl or halogen, $R^5$ has the meanings indicated for $R^4$ or is $COR^4$ or $CO_2R^4$, Ar is pyridyl, pyrimidyl, triazinyl, naphthyl or quinolinyl, where Ar may carry from one to four substituents selected from the group consisting of $OR^5$, $C_1-C_8$-alkyl, $C_2-C_6$-alkenyl, $C_2-C_6$-alkynyl, halogen, CN, $CO_2R^4$, $NO_2$, $SO_2R^4$, $SO_3R^4$, $NR^4R^5$, $SO_2NR^4R^5$, $SR^4$, $CF_3$, $CHF_2$, pyrrolyl and pyrrolidinyl, or a salt thereof with a physiologically tolerated acid.

2. The pyrimidine compound of formula I defined in claim 1, where

Ar is pyridyl, pyrimidyl, triazinyl, naphthyl or quinolinyl, where Ar may carry one or two substituents X and Y selected from the group consisting of $OR^5$, $C_1-C_8$- alkyl, halogen, CN, $CO_2R^4$, $NO_2$, $SO_2R^4$, $SO_3R^4$, $NR^4R^5$, $SO_2NR^4R^5$, $SR^4$, $CF_3$, $CHF_2$, and or a salt thereof with a physiologically tolerated acid.

3. The pyrimidine compound of formula I defined in claim 1, where A is $C_3-C_{10}$-alkylene which is interrupted by, or which is bonded to the pyrimidine ring through the radical $NR^4$, or a salt thereof with a physiologically tolerated acid.

4. The pyrimidine compound of formula I defined in claim 1, where $R^1$, $R^2$ and $R^3$ are, independently from one another, H, $C_1-C_8$-alkyl, which may be unsubstituted or substituted by OH, $OC_1-C_8$-alkyl or halogen, or OH, $OC_1-C_8$- alkyl, $SR^4$ or $NR^4R^5$ where $R^4$ and $R^5$ are, independently of one another, H or $C_1-C_8$-alkyl;

Ar is pyridyl or pyrimidyl, where Ar may carry one to four substituents selected from the group consisting of $C_1-C_8$-alkyl, or $OR^5$ where $R^5$ is H, $C_1-C_8$-alkyl, which may be unsubstituted or substituted by OH, $OC_1-C_8$-alkyl or halogen, or $CF_3$, $CHF_2$, halogen, $C_2-C_6$-alkenyl, $C_2-C_6$-alkynyl, $C_5-C_6$-cycloalkyl, phenyl, or a salt thereof with a physiologically tolerated acid.

5. The pyrimidine compound of formula I defined in claim 4, where B is

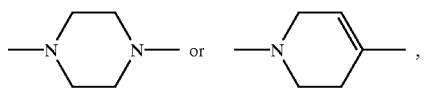

or a salt thereof with a physiologically tolerated acid.

6. The pyrimidine compound of formula I defined in claim 4, where $R^1$ is H, $C_1-C_8$-alkyl which is unsubstituted or substituted by OH, $OC_1-C_8$-alkyl or halogen, or $OR^4$, $SR^4$ or $NR^4R^5$ where $R^4$ and $R^5$ are, independently of one another, H or $C_1-C_8$-alkyl, $R^2$ is H, $OR^4$ or $C_1-C_8$-alkyl, and $R^3$ is H, or a salt thereof with a physiologically tolerated acid.

7. The pyrimidine compound of formula I defined in claim 1, where

Ar is pyridinyl which may carry from one to four substituents selected from the group consisting of $C_1-C_8$- alkyl, phenyl, OH, $OC_1-C_8$-alkyl, halogen, $CF_3$, CN, $C_2-C_6$-alkenyl and $C_2-C_6$-alkynyl, or a salt thereof with a physiologically tolerated acid.

8. The pyrimidine compound of formula I defined in claim 1, where

Ar is pyrimidinyl which may carry from one to three substituents selected from the group consisting of $C_1-C_8$-alkyl, phenyl, $C_5-C_6$-cycloalkyl, OH, $OC_1-C_8$- alkyl, halogen, CN, $NO_2$, $CF_3$, $CHF_2$, and $SO_2R^4$ or $SR^4$ where $R^4$ is H or $C_1-C_8$-alkyl, or a salt thereof with a physiologically tolerated acid.

9. The pyrimidine compound of formula I defined in claim 8, where Ar is

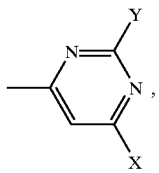

wherein X and Y are, independently of one another, selected from the group consisting of $C_1$–$C_8$-alkyl, or phenyl, pyrrolyl, CN, $NO_2$, $CF_3$, $CHF_2$, $OC_1$–$C_8$-alkyl, halogen, $SO_2R^4$ or $SR^4$ where $R^4$ is H or $C_1$–$C_8$-alkyl, or
a salt thereof with a physiologically tolerated acid.

10. The pyrimidine compound of formula I defined in claim 9, where X and Y are, independently of one another, selected from the group consisting of $C_1$–$C_8$-alkyl, $CF_3$ and $CHF_2$, or a salt thereof with a physiologically tolerated acid.

11. The pyrimidine compound of formula I defined in claim 8, where B is

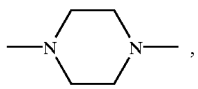

or a salt thereof with a physiologically tolerated acid.

12. The pyrimidine compound of formula I defined in claim 8, where $R^1$, $R^2$ and $R^3$ are independently selected from H, $C_1$–$C_8$-alkyl, or $OR^4$, wherein $R^4$ is H or $C_1$–$C_8$-alkyl, or a salt thereof with a physiologically tolerated acid.

13. A process for preparing the compound of claim 1, which comprises
i) reacting a compound of formula II:

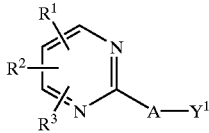

(II)

where $Y^1$ is a suitable leaving group, with a compound of formula III $$H-B-Ar \qquad (III)$$

ii) to prepare a compound of formula I' where A is interrupted by or is bonded to the pyrimidine ring through $NR^4$:

reacting a compound of formula:

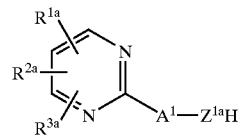

where
$R^{1a}$ is OH,
$R^{2a}$ and $R^{3a}$ are, independently of one another, H, $C_1$–$C_6$-alkyl, $OC_1$–$C_6$-alkyl, $SC_1$–$C_6$-alkyl, $CO_2H$, OH, $NR^4R^5$ or halogen, where $R^4$ and $R^5$ are H or $C_1$–$C_6$-alkyl,
$Z^{1a}$ is $NHR^4$ and
$A^1$ is $C_0$–$C_{15}$-alkylene, with a compound of formula VI:

$$Y^1-A^2-B-Ar \qquad (VI)$$

where $Y^1$ is a suitable leaving group, and $A^2$ is $C_1$–$C_{15}$-alkylene, where $A^1$ and $A^2$ together have 2 to 15 carbon atoms.

14. A pharmaceutical composition comprising the compound of formula I defined in claim 1 with or without physiologically acceptable vehicles and/or ancillary substances.

15. A method of treating schizophrenia, depression, neuroses and psychoses which respond to dopamine $D_3$ ligands, which comprises administering a therapeutically effective amount of the pyrimidine compound of formula I defined in claim 1 or its salt with a physiologically tolerated acid to a person requiring such treatment.

* * * * *